United States Patent
Imamura et al.

(10) Patent No.: US 6,872,788 B2
(45) Date of Patent: Mar. 29, 2005

(54) PRODUCTION METHOD OF POLYESTER CONTAINING EPOXY GROUP IN SIDE CHAIN AND PRODUCTION METHOD OF CROSSLINKED POLYMER

(75) Inventors: Takeshi Imamura, Kanagawa (JP); Etsuko Sugawa, Kanagawa (JP); Tetsuya Yano, Kanagawa (JP); Shin Kobayashi, Kanagawa (JP); Tsutomu Honma, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 112 days.

(21) Appl. No.: 10/427,919

(22) Filed: May 2, 2003

(65) Prior Publication Data
US 2004/0014937 A1 Jan. 22, 2004

Related U.S. Application Data

(63) Continuation-in-part of application No. 09/939,597, filed on Aug. 28, 2001, now abandoned.

(30) Foreign Application Priority Data

Aug. 31, 2000 (JP) ........................................ 2000-263508
Sep. 27, 2000 (JP) ........................................ 2000-294635

(51) Int. Cl.[7] .............................. C08F 20/00; C12P 7/62
(52) U.S. Cl. ...................... 525/440; 435/135; 435/142; 435/146; 435/874; 528/361; 525/440
(58) Field of Search .............................. 435/135, 142, 435/146, 874; 528/361; 525/440

(56) References Cited

U.S. PATENT DOCUMENTS

| 6,156,852 A | 12/2000 | Asrar et al. .................. 525/450 |
| 6,485,951 B2 | 11/2002 | Yano et al. .................. 435/190 |
| 6,492,147 B2 | 12/2002 | Imamura et al. ............. 435/135 |
| 6,521,429 B2 | 2/2003 | Honma et al. ............... 435/135 |
| 2001/0053544 A1 | 12/2001 | Yano et al. .................. 435/196 |
| 2001/0055795 A1 | 12/2001 | Yano et al. .................. 435/135 |
| 2002/0052444 A1 | 5/2002 | Imamura et al. ............. 525/107 |
| 2002/0098565 A1 | 7/2002 | Yano et al. .................. 435/196 |
| 2002/0160467 A1 | 10/2002 | Honma et al. ............... 435/135 |

FOREIGN PATENT DOCUMENTS

| EP | 0 274 151 A2 | 7/1988 |
| EP | 1 113 033 | 7/2001 |
| EP | 1 113 076 A2 | 7/2001 |
| JP | 5-159 | 1/1993 |

Primary Examiner—Samuel A. Acquah
(74) Attorney, Agent, or Firm—Fitzpatrick, Cella, Harper & Scinto

(57) ABSTRACT

A method is provided which biosynthesizes a PHA having an epoxy group on a side chain with improved physicochemical properties. Specifically, a method of producing a polyester containing an epoxy group in a side chain thereof using alkene as a raw material is provided which comprises the steps of bringing alkene into contact with a microorganism having an ability to uptake alkene and convert it to a polyester and allowing the microorganism to convert the alkene into a polyester containing an epoxy group in a side chain thereof. Further, a method of producing a crosslinked polymer is provided which comprises reacting the polyester obtained by the above mentioned method with a diamine compound.

18 Claims, 11 Drawing Sheets

US 6,872,788 B2

PRODUCTION METHOD OF POLYESTER CONTAINING EPOXY GROUP IN SIDE CHAIN AND PRODUCTION METHOD OF CROSSLINKED POLYMER

This application is CIP of Ser. No. 09/939,597, filed Aug. 28, 2001, now abandoned.

BACKGROUND OF THE INVENTION

1. Field of the Invention

The present invention relates to a method of producing a polyester using a microorganism.

2. Related Background Art

So far, it has been reported that a variety of microorganisms produce poly(3-hydroxybutyrate) (hereinafter, abbreviated as PHB) or other polyhydroxyalkanoates (PHA) and store it in their bodies ("Biodegradable plastic handbook", Biodegradable Plastic Study Associate edition, N.T.S Co., Ltd., pp. 178–197, 1995). These polymers can be utilized for production of various types of products by melt processing or the like, as is the case with conventional plastics. Further, they are biodegradable and therefore have an advantage that they can completely be decomposed by microorganisms in nature, and unlike conventional many synthetic polymeric compounds, they do not remain in natural environments to cause environmental pollution and may not generate harmful substances such as dioxins, endocrine disrupting chemical substances, etc. since they are not required to be incinerated. Furthermore, they are excellent in biocompatibility and highly expected to be applied to the use as soft members for medical care (Japanese Patent Application Laid-Open No. 5-000159).

Recently, in the industrial application of such PHA, it has been attempted to extend the diversity in the physicochemical characteristics of PHA by producing PHA composed of units different from common monomer units.

As one of such methods, an attempt has been made to improve the physicochemical properties of PHA by introducing epoxy groups in side chains of PHA and carrying out a crosslinking reaction or chemical modification using the introduction sites as active points.

There is reported in Macromolecules, 31, pp. 1480–1486 (1998) and Journal of Polymer Science: Part A: Polymer Chemistry, 36, pp. 2381–2387 (1998), synthesis of PHA containing epoxy groups in the side chain terminals by culturing *Pseudomonas oleovorans* in culture media containing sodium octanoate and 10-undecenoic acid as an unsaturated fatty acid in various ratios to produce PHA containing a variety of percentages of units with unsaturated bonds in the terminals of the side chains and then chemically epoxidizing the unsaturated sites with 3-chlorobenzoic acid. Further, there is reported in Journal of Polymer Science: Part A: Polymer Chemistry, 36, pp. 2389–2396 (1998) that a crosslinking reaction of the above described epoxy PHA was carried out with succinic anhydride using 2-ethyl-4-methylimidazole as an initiator.

As described above, in the improvement of the physicochemical properties of PHA, epoxy groups of the side chain terminals are very useful, however, there is no synthesis method other than the chemical epoxidation of the unsaturated sites in the side chain terminals, and such chemical epoxidation requires very complicated operations and has therefore a practical disadvantage in terms of cost.

SUMMARY OF THE INVENTION

It is, therefore, an object of the present invention to provide a method for solving the above described problems.

According to a first aspect of the present invention, there is provided a method of producing a polyester that contains an epoxy group in a side chain thereof using an alkene compound as a raw material, comprising the steps of bringing an alkene compound into contact with a microorganism having an ability to uptake the alkene compound and convert it to a polyester and allowing the microorganism to convert the alkene compound into a polyester containing an epoxy group in a side chain thereof.

In the present invention, it is preferred that the method comprises the step of culturing the microorganism in a culture medium containing alkene.

In the present invention, it is also preferred that the method further comprises the step of isolating the polyester produced by the microorganism.

In the present invention, it is further preferred that the isolation step comprises recovering the polyester from the cell of the microorganism.

According to a second aspect of the present invention, there is provided a method of producing a crosslinked polymer comprising reacting the polyester obtained by the above mentioned method with a diamine compound.

DETAILED DESCRIPTION OF THE PREFERRED EMBODIMENTS

The polyester obtained according to the method of the present invention comprises monomer units having epoxy in the side chain thereof. When a 1-alkene compound is used as a raw material, the polyester obtained according to the method of the present invention contains at least 1 mol % of a unit represented by the chemical formula (1):

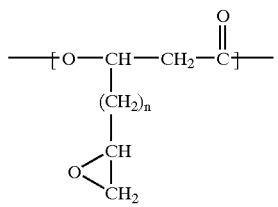

(1)

(wherein n is an integer of 1 to 7) in monomer units thereof.

The polyester obtained according to the method of the present invention may further contain at least 1 mol % of a unit represented by the chemical formula (2):

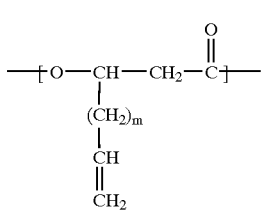

(2)

(wherein m is an integer of 1 to 7) in monomer units thereof.

The polyester obtained according to the method of the present invention may further contain at least 1 mol % of a unit represented by the chemical formula (3):

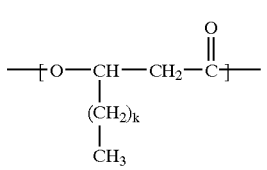

(3)

(wherein k is an integer of 0 to 8) in monomer units thereof.

The alkene compound to be used as a raw material in the method of the present invention, e.g., 1-alkene, is preferably a 1-alkene with 7 to 12 carbons, namely 1-heptene, 1-octene, 1-nonene, 1-decene, 1-undecene, and 1-dodecene.

Further, the number-average molecular weight of the polyester obtained by the present invention is 10,000 to 1,000,000 and more particularly 10,000 to 500,000.

<Microorganism>

The microorganism to be used for the method of the present invention is a microorganism having an ability to epoxidize an alkene compound and convert it to a corresponding epoxyalkane compound; an ability to convert a terminal of the epoxyalkane compound to form an epoxidized carboxylic acid; and an ability to convert the epoxidized carboxylic acid to a polyester and includes microorganisms belonging to *Pseudomonas* species and more particularly includes *Pseudomonas cichorii* YN2 strain; FERM BP-7375 used in the examples of the present invention as described below.

*Pseudomonas cichorii* YN2; FERM BP-7375 as a microorganism used for the present invention is a microorganism having the following properties and deposited to International Patent Organism Depositary in National Institute of Advanced Industrial Science and Technology, AIST (deposition number: FERM BP-7375).

The mycological properties of the YN2 strain are as follows.

Figure 1:
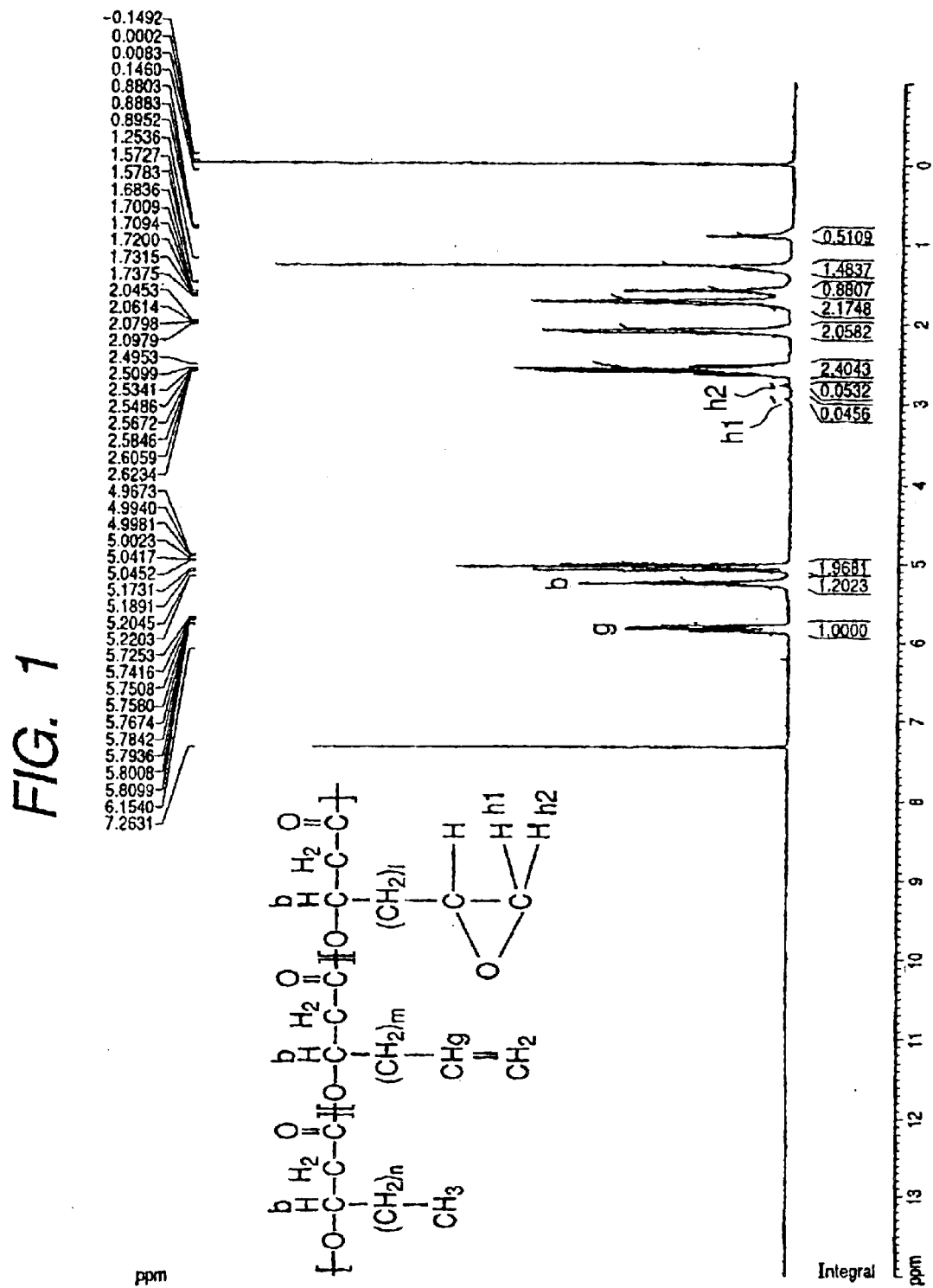
FIG. 1 is a graphical representation showing 1H-NMR of the polymer obtained in Example 1.
Figure 2:
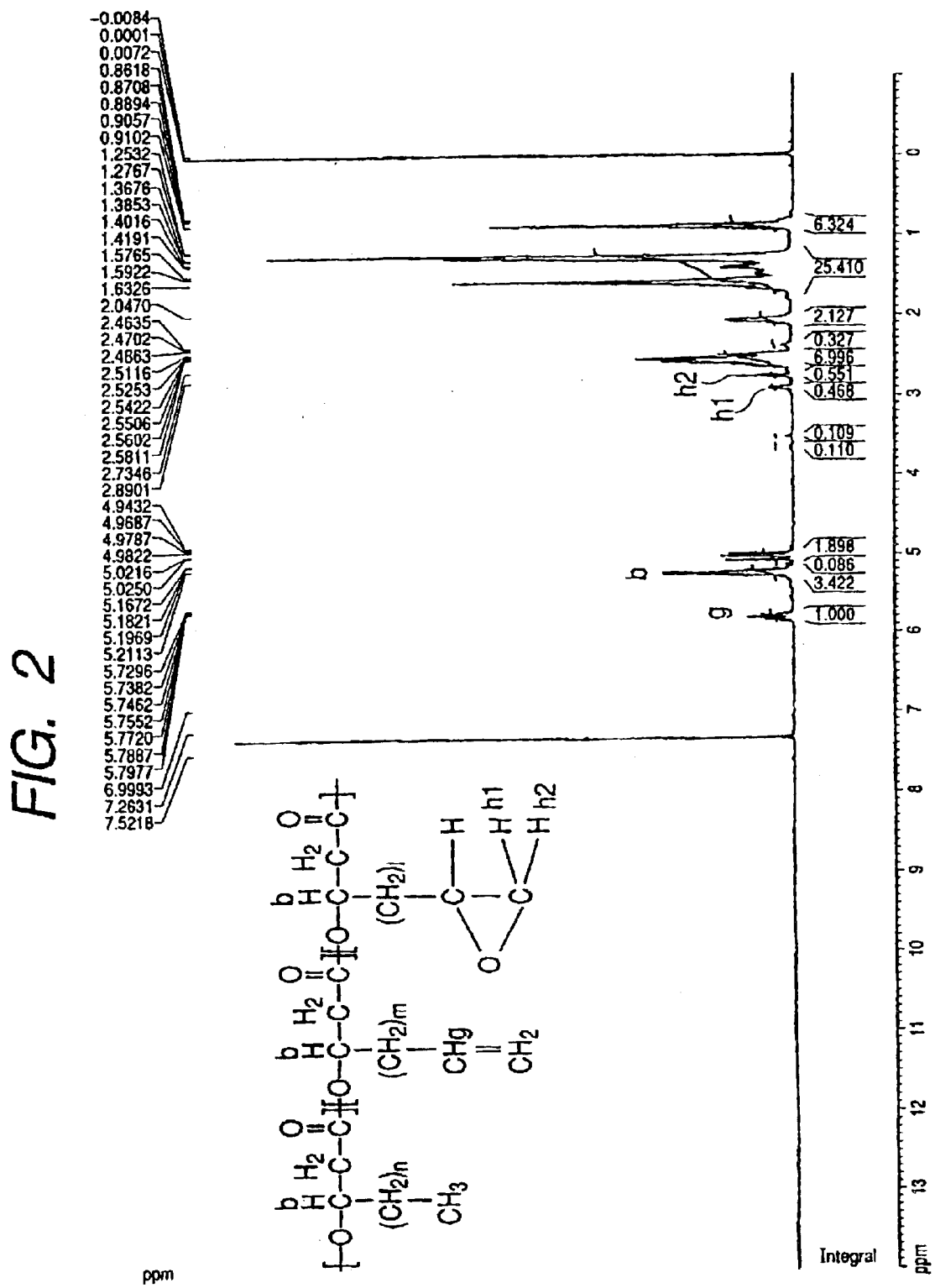
FIG. 2 is a graphical representation showing 1H-NMR of the polymer obtained in Example 2.
Figure 3:
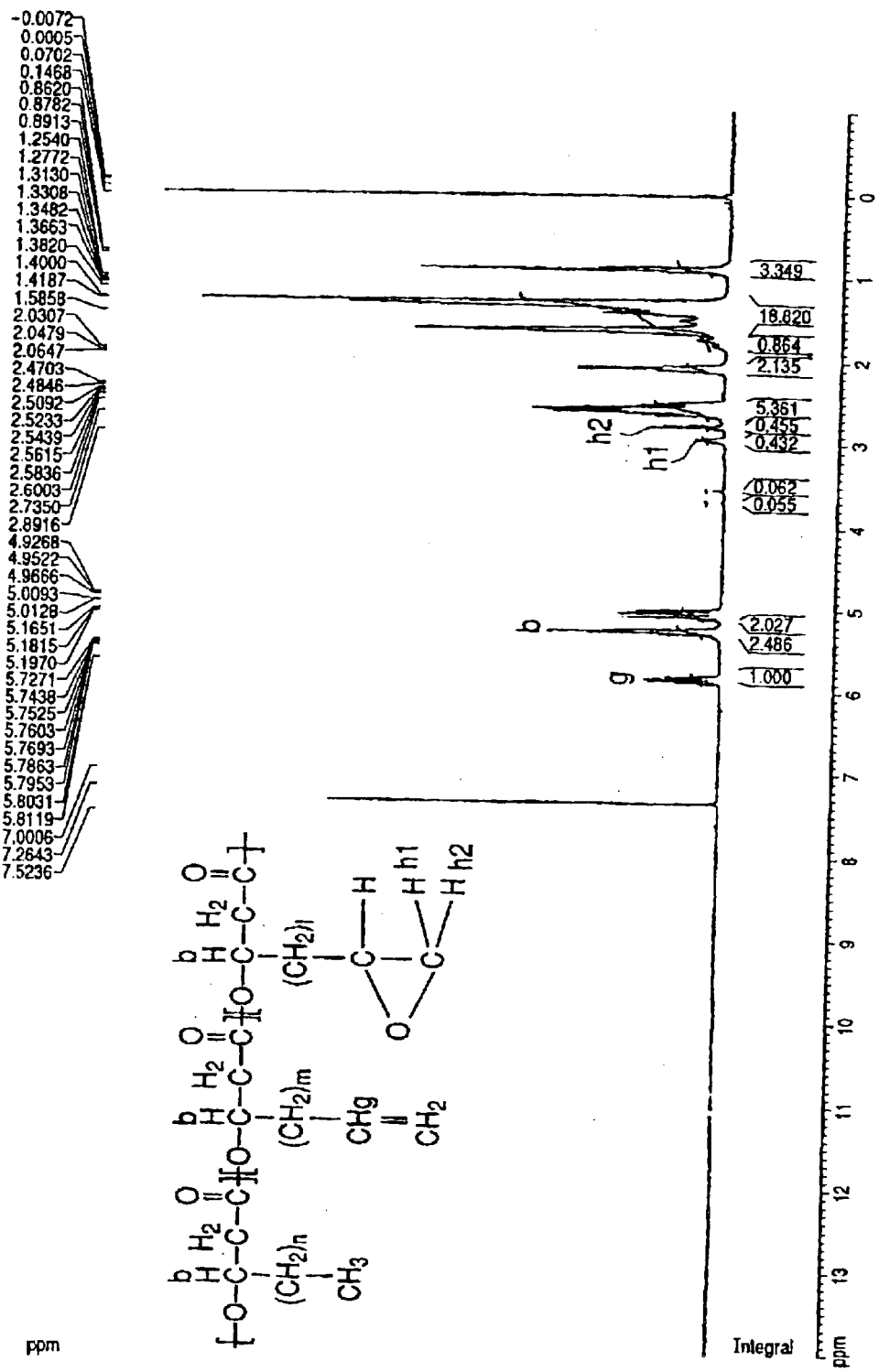
FIG. 3 is a graphical representation showing 1H-NMR of the polymer obtained in Example 3.
Figure 4:
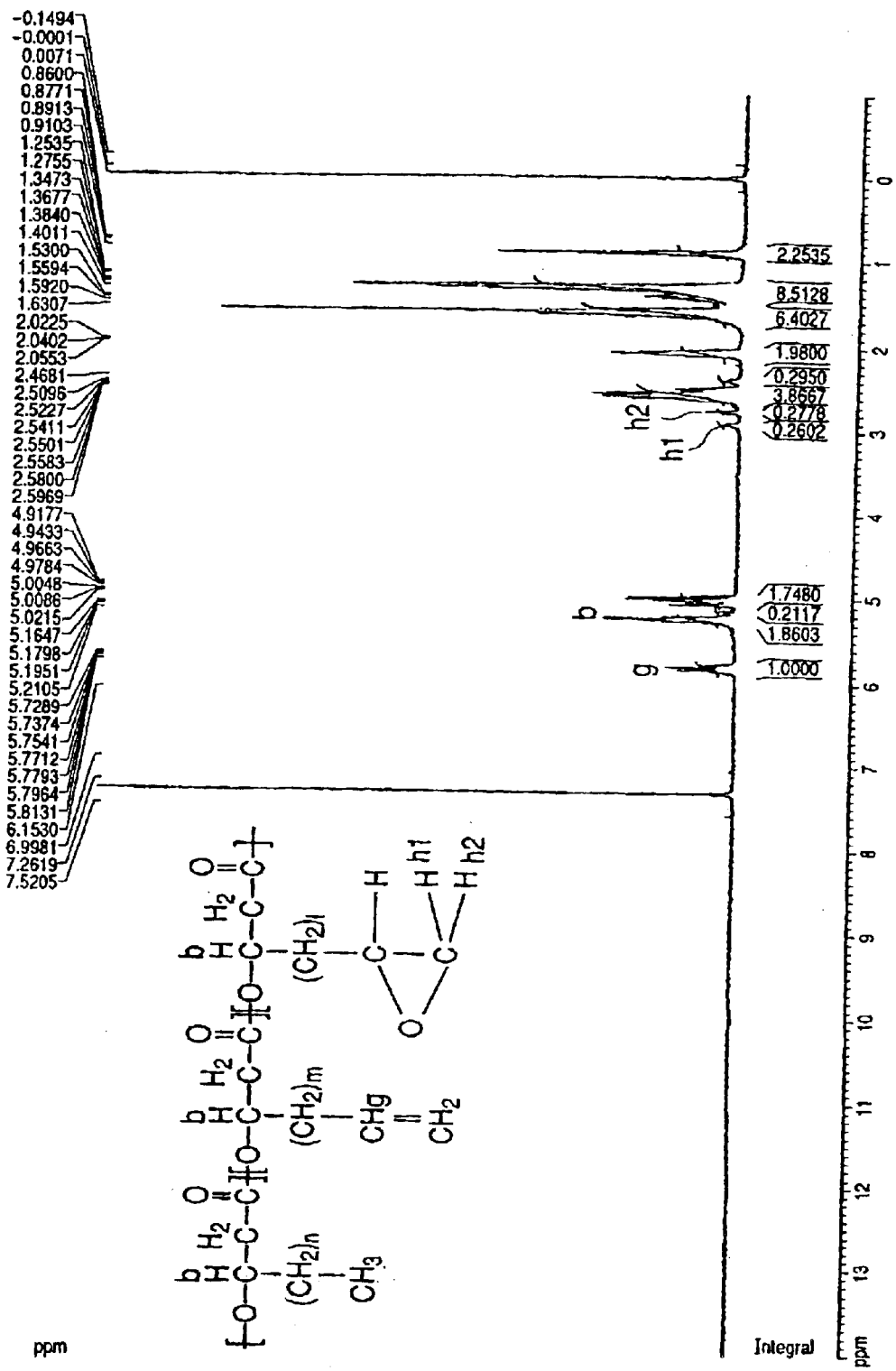
FIG. 4 is a graphical representation showing 1H-NMR of the polymer obtained in Example 4.
Figure 5:
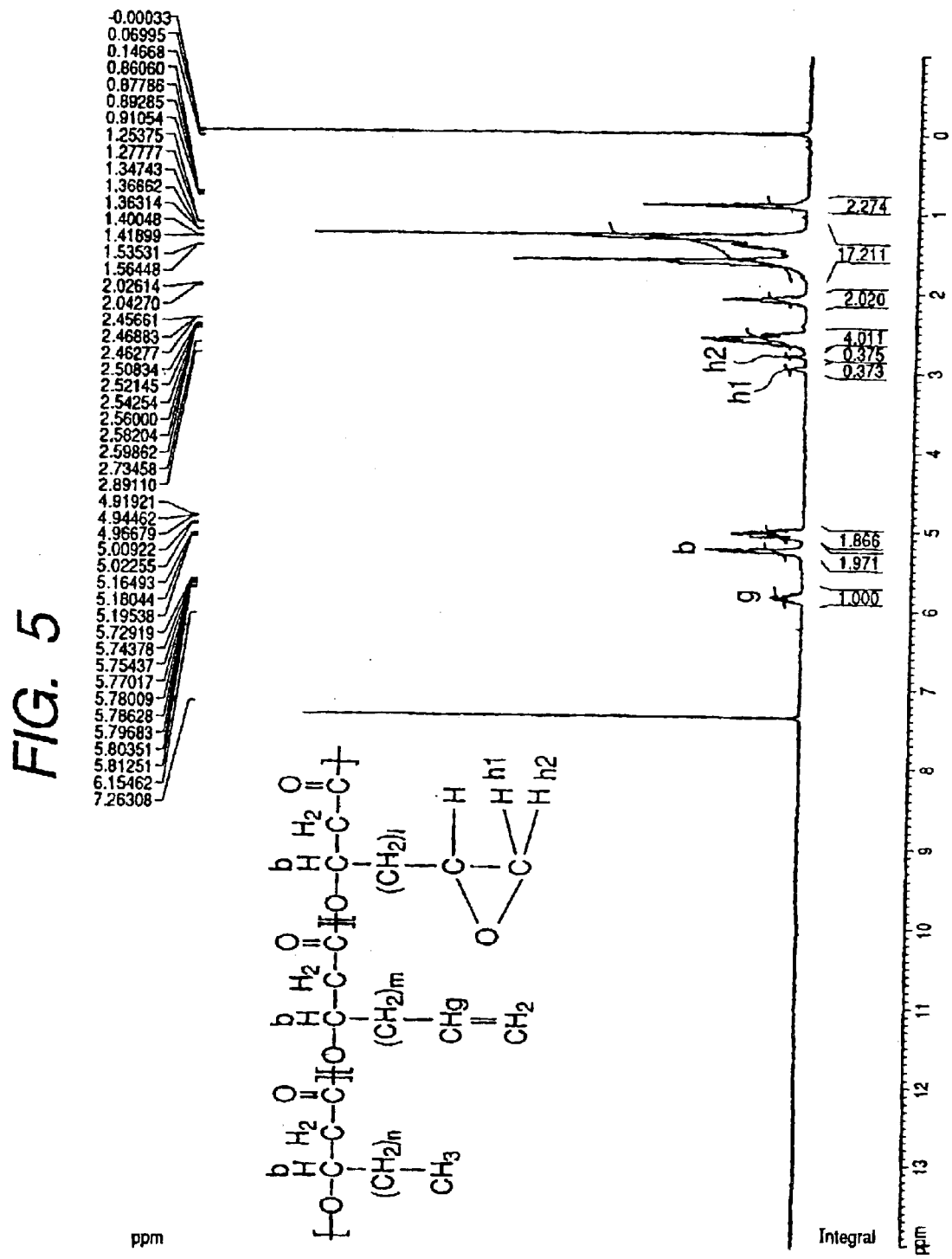
FIG. 5 is a graphical representation showing 1H-NMR of the polymer obtained in Example 5.
Figure 6:
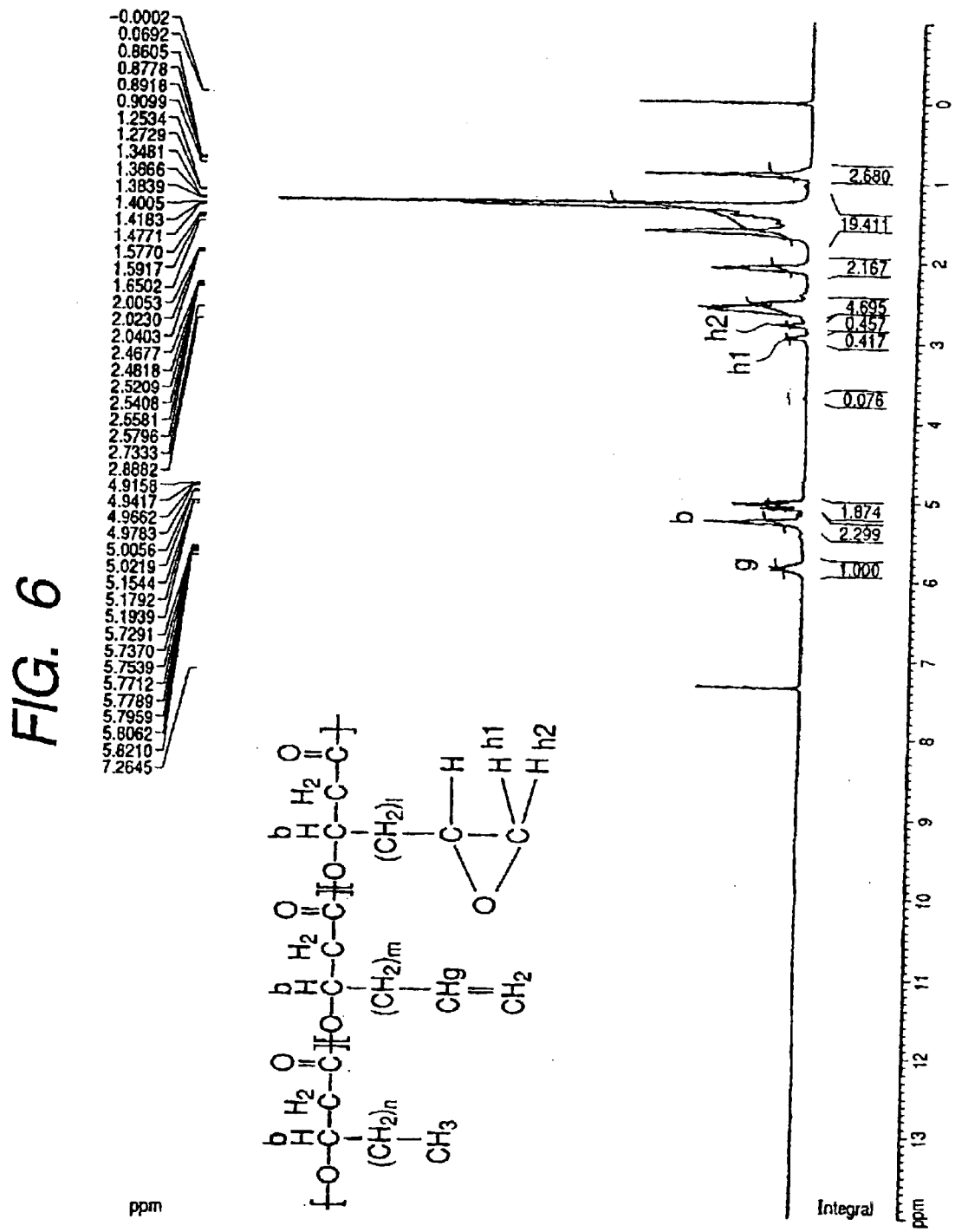
FIG. 6 is a graphical representation showing 1H-NMR of the polymer obtained in Example 6.
Figure 7:
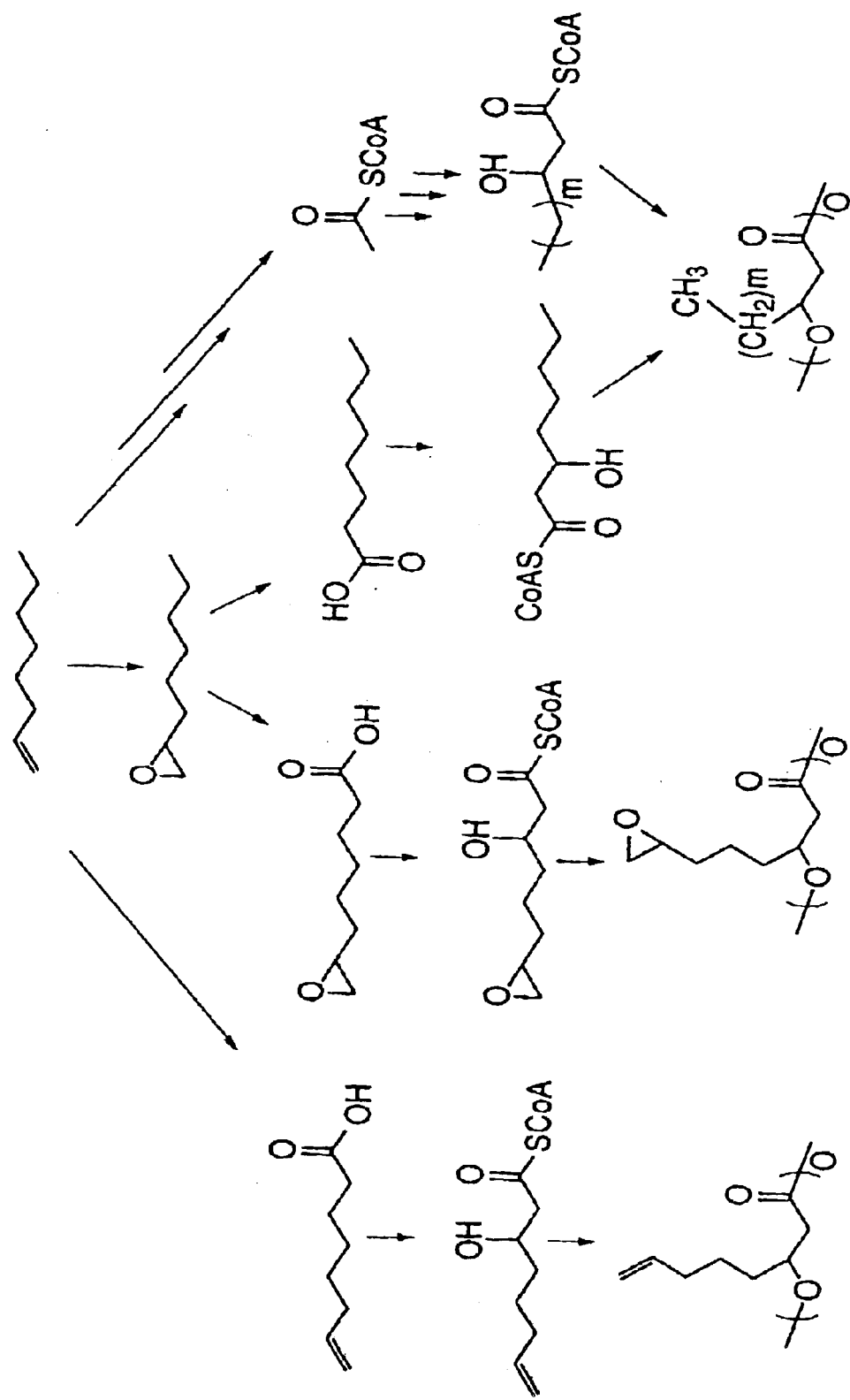
FIG. 7 is a scheme showing the routes of polymer production from 1-alkene using YN2 strain.

(1) Morphological Properties culture temperature: 30° C.
cell shape: rod, 0.8 $\mu$m×1.5 to 2.0 $\mu$m
Gram staining: negative
sporulation: negative
motility: positive
colony shape: circular; entire, smooth margin; low convex; smooth surface; glossy; translucent (2) Physiological Properties catalase: positive
oxidase: positive
O/F test: non-fermentative
nitrate reduction: negative
indole production: positive
glucose oxidation: negative
arginine dihydrolase: negative
urease: negative
esculin hydrolysis: negative
gelatin hydrolysis: negative
β-galactosidase: negative
fluorescent pigment production on King's B agar: positive,
growth under 4% NaCl: positive (weak growth)
poly-β-hydroxybutyrate accumulation: negative(*)
Tween 80 hydrolysis: positive
* determined by staining colonies cultured on nutrient agar with Sudan Black (3) Substrate Assimilation glucose: positive
L-arabinose: positive
D-mannose: negative
D-mannitol: negative
N-acetyl-D-glucosamine: negative
maltose: negative
potassium gluconate: positive
n-caprate: positive
adipate: negative
dl-malate: positive
sodium citrate: positive
phenyl acetate: positive This bacterial strain is also a microorganism disclosed in Japanese Patent Application No. 11-371863. This bacterial strain has a capability of epoxidizing alkene to an corresponding epoxyalkane as will be described in the examples below. Generally, the enzyme for exhibiting such a capability is an alkene-monooxygenase. It is highly probable that this bacterial stain also has the alkene-monooxygenase. Further, this bacterial strain has not been found to produce an epoxyalkanoic acid from a corresponding alkenoic acid. Based on the results deduced from the above described matter, it is implied that the route of the polyester production of the present invention by this bacterial stain is those shown in FIG. 7 when 1-alkene is used.

<Culture Process>

Any culture may be usable as a culture to be employed for the present invention as long as it is an inorganic salt culture containing phosphate and a nitrogen source such as an ammonium salt or a nitrate and it is possible to improve the productivity of PHA by adjusting the concentration of the nitrogen source. Since the alkene compound to be added has a low solubility in water and is highly volatile, it is required to supply the alkene in a gas state during the culture and to put it in sealed state while ensuring oxygen which the microorganism requires.

The composition of a culture employed for one embodiment of the method of the present invention as an example of an inorganic salt culture is shown below.
(M9 Culture)

Na$_2$HPO$_4$: 6.3
KH$_2$PO$_4$: 3.0
NH$_4$Cl: 1.0
NaCl: 0.5 g/L, pH=7.0

(1/10N-M9 Culture)

Na$_2$HPO$_4$: 6.3
KH$_2$PO$_4$: 3.0
NH$_4$Cl: 0.1
NaCl: 0.5g/L, pH=7.0

Further, in order to maintain good proliferation and PHA productivity, it is required to add the following solution of the trace amount components in about 0.3% (v/v) to the above described inorganic salt culture:

(Trace Amount Component Solution)

nitrilo triacetate: 1.5; MgSO$_4$: 3.0;
MnSO$_4$: 0.5; NaCl: 1.0;
FeSO$_4$: 0.1; CaCl$_2$: 0.1;
CoCl$_2$: 0.1; ZnSO$_4$: 0.1;
CuSO$_4$: 0.1; AlK(SO$_4$)$_2$: 0.1;
H$_3$BO$_3$: 0.1; Na$_2$MoO$_4$: 0.1; and
NiCl$_2$: 0.1 (unit: g/L)

The culture temperature may be any temperature at which good prolification of the above described bacterial strain can be assured and it is preferably about 20° C. to 30° C.

Any culture method including a liquid culture method, a solid culture method, etc. can be employed as long as it is suitable for proliferation of the microorganism and production of PHA. Further, the type of the culture includes, but not limited to, a batch culture, a fed-batch culture, a semi-continuous culture, and a continuous culture.

A commonly employed method can be employed for obtaining PHA from the culture substances containing cultured cells of the present invention and the culture liquid. In the case where PHA is secreted into the culture liquid, a method for extraction and purification from the culture liquid is employed and in the case where PHA is accumulated in the cells, a method for extraction and purification from the cells is employed. For example, for recovering PHA from the cultured cells of the microorganism, chloroform extraction, which is commonly employed, is most convenient, however in the environments where an organic solvent is troublesome to be used, there can be employed a method of recovering only PHA by removing other components in cells other than PHA by treatment with a surfactant such as SDS, etc., treatment with an enzyme such as lysozyme, etc., treatment by chemicals such as EDTA, sodium hypochlorite, ammonia, etc.

Incidentally, there is reported in Appl. Environ. Microbiol., 54, pp. 2924–2932 (1998) production of a polyester using Pseudomonas oleovorans similar to the method of the present invention, however the polyester produced therein has no epoxy groups in the side chains but contains both units having double bonds in terminals of side chains and units having saturated alkylene chains as side chains.

The polymer obtained according to the method of the present invention can be subjected to chemical conversion, as with common polymers having epoxy groups. More particularly, the chemical conversion includes a crosslinking reaction with hexamethylene-diamine, succinic anhydride, or 2-ethyl-4-methylimidazole, or electron beam irradiation. Further, it is also possible to convert it into hydroxyl groups or to introduce sulfone groups thereinto. Furthermore, it is also possible to add a compound having thiol or amine thereto.

The present invention further provides a method of producing a crosslinked polymer by reacting the above mentioned polyester with a diamine compound. More particularly, the present invention provides a method of producing a crosslinked polymer by reacting the above mentioned polyester with hexamethylenediamine. Such a reaction proceeds along a reaction route as shown in the following scheme to produce a crosslinked polymer.

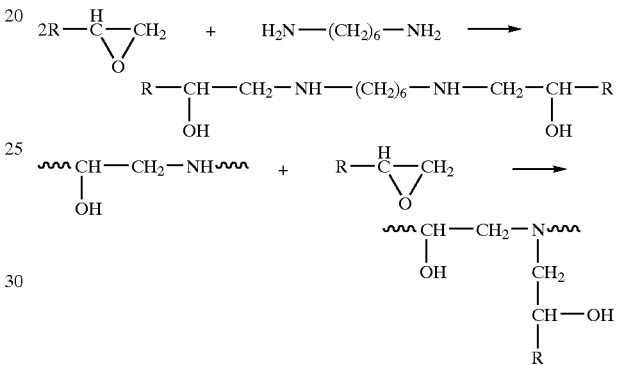

The reaction temperature is preferably 50° C. to 120° C. and the reaction time is preferably within the range of 10 minutes to 120 minutes.

Thereinbefore the present invention was described with 1-alkene, but the present invention also works with other alkene compounds as shown in Examples 10 and 11 below.

<EXAMPLES>

Now, examples will be described, but the present invention is not limited to the examples.

Example 1

Colonies of YN2 strain on the M9 agar culture containing 0.1% of yeast extract were suspended in a sterilized physiological saline solution to OD (600 nm)=1.0. The resulting suspension was spread onto 20 plates of 1/10N-M9 agar medium free from C sources and static cultivation was carried out at 30° C. in a 1-heptene atmosphere.

After 4 days, cells were combined together, cleaned with methanol, collected by centrifugal separation, and dried in vacuum.

To the dried cells, 50 mL of chloroform was added and stirred at 30° C. for 48 hours to extract PHA. The chloroform layer was then filtered and concentrated by an evaporator, which was then added to cold methanol and the precipitate was recovered and dried in vacuum.

Example 2

A production experiment was carried out in the same manner as in Example 1 except that 1-heptene was changed to 1-octene.

Example 3

A production experiment was carried out in the same manner as in Example 1 except that 1-heptene was changed to 1-nonene.

Example 4

A production experiment was carried out in the same manner as in Example 1 except that 1-heptene was changed to 1-decene.

Example 5

A production experiment was carried out in the same manner as in Example 1 except that 1-heptene was changed to 1-undecene.

Example 6

A production experiment was carried out in the same manner as in Example 1 except that 1-heptene was changed to 1-dodecene.

The weights of the cells and dried polymers obtained in Example 1 to 6 were shown in Table 1 below.

TABLE 1

| Example No. | Dry weight of cells (mg) | Dry weight of polymer (mg) |
|---|---|---|
| 1 | 160 | 48 |
| 2 | 170 | 52 |
| 3 | 160 | 55 |
| 4 | 180 | 58 |
| 5 | 170 | 55 |
| 6 | 160 | 48 |

(Analysis and Evaluation)

Analysis of the units of the polymer obtained in Examples 1 to 6 was carried out as follows. That is, about 10 mg of PHA was put in an eggplant type flask of 25 mL capacity and dissolved in 2 mL of chloroform, and 2 mL of a methanol solution containing 3% of sulfuric acid was added thereto and a reaction was effected at 100° C. for 3.5 hours under reflux. After completion of the reaction, 10 mL of deionized water was added and the resulting mixture was shaken vigorously for 10 minutes, and an underlying chloroform layer of two separated layers was taken out, dehydrated with magnesium sulfate and subjected to a gas chromatographic mass spectrograph (GC-MS, Shimadzu QP-5050 model, EI method) to identify the methyl ester of PHA monomer units. The results of area % of total ion chromatogram (TIC) were shown in Table 2. In this case, since the monomer units were converted by methanolysis, no epoxy unit was detected.

TABLE 2

| Unit | Example No. | | | | | |
|---|---|---|---|---|---|---|
| | 1 | 2 | 3 | 4 | 5 | 6 |
| C4 | 0.5 | — | — | — | — | — |
| C5 | 2.0 | — | — | — | — | — |
| C6 | 0.7 | 5.3 | 1.3 | 3.0 | 1.4 | 2.2 |
| C6= | — | 0.9 | — | 1.3 | — | 0.7 |
| C7 | 7.8 | 12.7 | 6.9 | 4.5 | 3.9 | 2.5 |
| C7= | 87.2 | 2.2 | 5.2 | 1.3 | 2.3 | — |
| C8 | — | 29.4 | 17.3 | 13.3 | 8.7 | 9.8 |
| C8= | — | 38.5 | — | 28.1 | 12.8 | 19.4 |
| C9 | — | — | 24.5 | 9.7 | 12.5 | 5.7 |
| C9= | — | — | 43.6 | — | 15.8 | — |
| C10 | 1.8 | 5.4 | 1.2 | 11.4 | 10.6 | 10.3 |
| C10= | — | — | — | 27.4 | 18.5 | 24.0 |
| C11 | — | — | — | — | 3.6 | 3.5 |
| C11= | — | — | — | — | 9.9 | — |
| C12 | — | 1.9 | — | — | — | 5.7 |
| C12= | — | 3.5 | — | — | — | 15.3 |

In Table 2, the symbols used for representing the units have the following meaning.

C4: 3-hydroxybutyric acid; C5: 3-hydroxyvaleric acid; C6: 3-hydroxyhexanoic acid; C6=: 3-hydroxy-5-hexenoic acid; C7: 3-hydroxyheptanoic acid; C7=: 3-hydroxy-6-heptenoic acid; C8: 3-hydroxyoctanoic acid; C8=: 3-hydroxy-7-octenoic acid; C9: 3-hydroxynonanoic acid; C9=: 3-hydroxy-8-nonenoic acid; C10: 3-hydroxydecanoic acid; C10=: 3-hydroxy-9-decenoic acid; C11: 3-hydroxyundecanoic acid; C11=: 3-hydroxy-10-undecenoic acid; C12: 3-hydroxydodecanoic acid; and C12=: 3-hydroxy-11-dodecenoic acid.

The polymers obtained in Examples 1 to 6 were subjected to 1H-NMR analysis (Analyzer: FT-NMR: Bruker DPX400; Determined nuclide: 1H; Solvent used: heavy chloroform with TMS). The attribution of protons of methine in side chain terminals, double bonds in side chain terminals, and epoxy groups was determined according to the method described in Macromolecules, 31, pp. 1480–1486 (1998). The spectra thus obtained were shown in FIGS. 1 to 6.

The mol % of respective units of saturated side chain, unsaturated side chain (having double-bond at terminal), or epoxidized side chain at terminal were calculated based on the above described results and shown in Table 3.

TABLE 3

| Example | Saturated | Unsaturated | Epoxidized |
|---|---|---|---|
| 1 | 12.5 | 83.3 | 4.2 |
| 2 | 55.9 | 29.4 | 14.7 |
| 3 | 44.0 | 40.0 | 16.0 |
| 4 | 31.6 | 52.6 | 15.8 |
| 5 | 30.0 | 50.0 | 20.0 |
| 6 | 39.1 | 43.5 | 17.4 |

Further, the molecular weights of the polymers obtained in Examples 1 to 6 were evaluated by GPC (Tosoh Corporation HLC-8020; Column: Polymer Laboratory, PL gel MIXED-C (5 μm); Solvent: chloroform; Converted on basis of polystyrene). The results were shown in Table 4.

TABLE 4

| Example | Number-average molecular weight (Mn) × $10^5$ | Weight-average molecular weight (Mw) × $10^5$ |
|---|---|---|
| 1 | 1.9 | 5.2 |
| 2 | 2.5 | 5.5 |
| 3 | 2.6 | 5.3 |
| 4 | 1.9 | 5.4 |
| 5 | 1.9 | 5.4 |
| 6 | 2.0 | 4.9 |

Example 7

YN2 strain was cultured at 30° C. for 24 hours in a culture medium containing 0.5% polypeptone, and the cells were collected by centrifugal separation and again suspended in an inorganic salt culture medium. 10 mL of the resulting cell suspension was put in a vial of 27 mL capacity and sealed with a butyl rubber plug and an aluminum seal, and air containing 1-hexene gas was added thereto with a syringe. As a control, a sample only of an inorganic salt culture medium containing no YN2 strain was prepared in the same manner and the respective vials were shaken at 30° C. for 1 hour. After the shaking, 0.1 mL of a vapor phase in each vial was withdrawn by a syringe and subjected to a gas chromatographic (GC) analysis. The conditions of the GC were as follows.

Figure 8A:
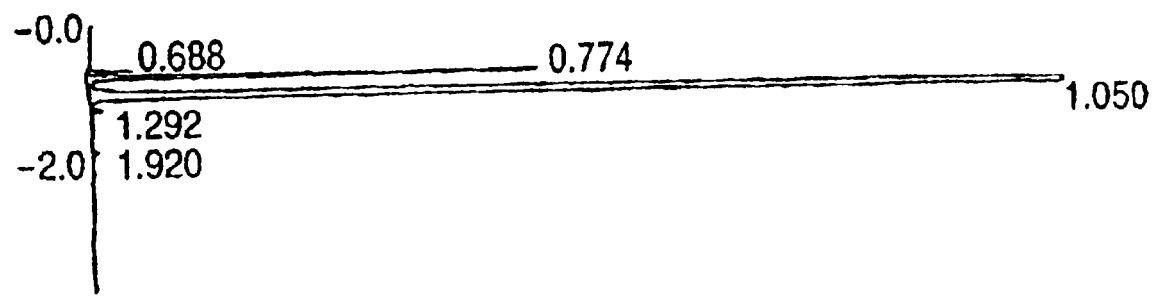
FIGS. 8A, 8B and 8C are views each showing a GC chart of the result described in Example 7.
Figure 8B:
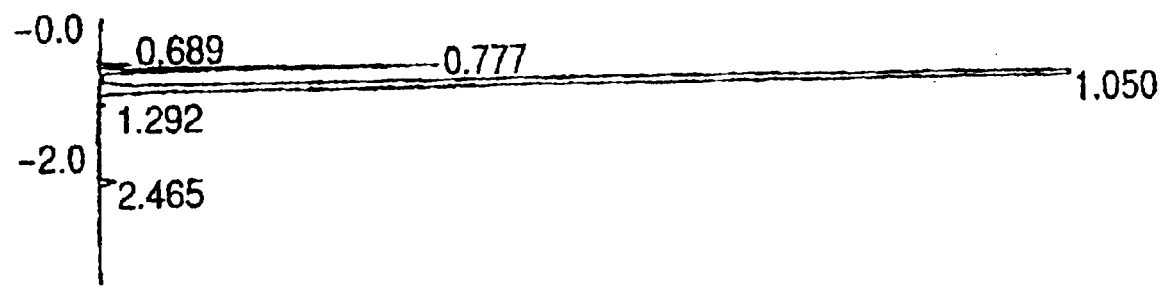
Figure 8C:
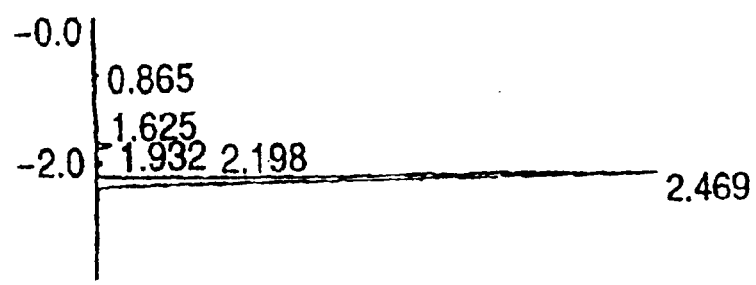

Analyzer: Shimadzu GC-14B; Column: DB-624 (mfd. by J & W Co.); Column temperature: constantly 100° C.; Injector /detector temperature: 230° C.; Detector: FID The results are shown in FIGS 8A to 8C. FIG. 8A shows the results of the sample only of the inorganic salt culture medium containing no YN2 strain. A peak of 1-hexene is observed near 1.05. FIG. 8B shows the results of the sample of the cell suspension of YN2 strain. A peak, which is not observed in FIG. 8A, is observed near 2.47. FIG. 8C shows the results of a sample of a standard sample of 1,2-epoxyhexane. A peak corresponding to the above mentioned peak is observed near 2.47. According to the results, it was made clear that the YN2 strain converted 1-hexene to 1,2-epoxyhexane.

Example 8

Figure 9A:
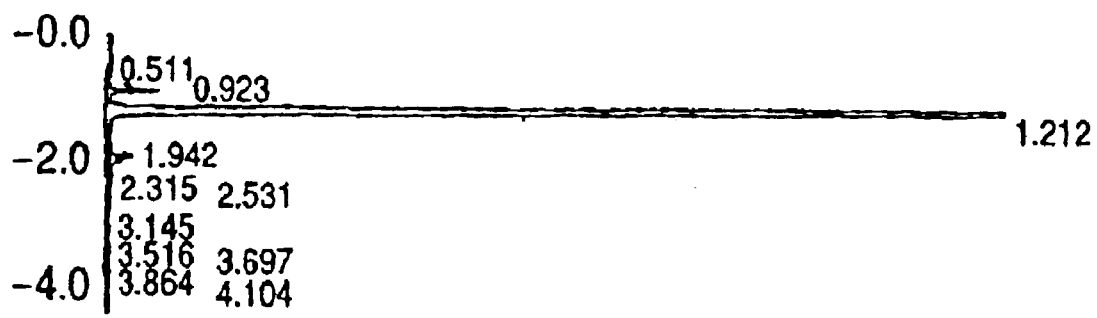
FIGS. 9A, 9B and 9C are views each showing a GC chart of the result described in Example 8.
Figure 9B:
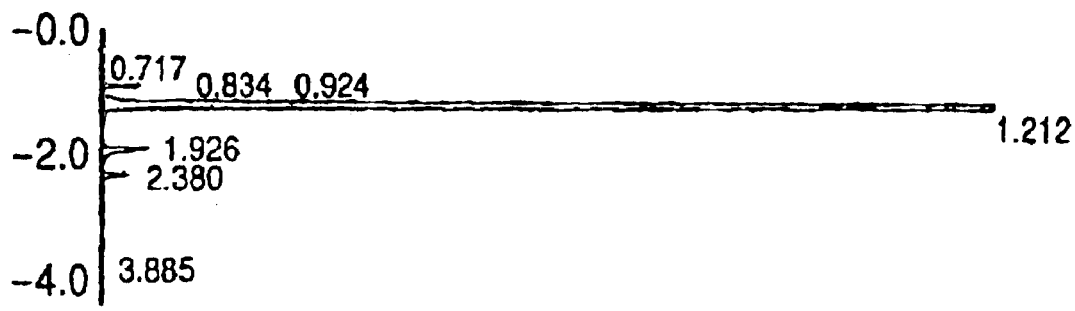
Figure 9C:
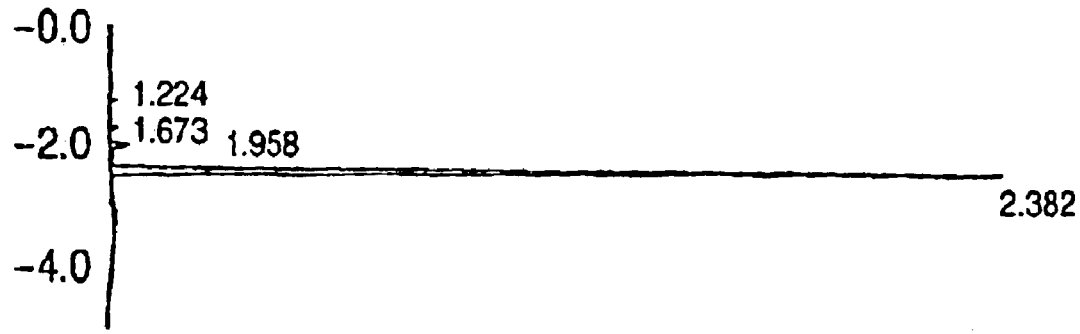

The conversion activity of YN2 strain to 1-octene was evaluated in the same manner as in Example 7 (GC column temperature: 150° C.). The results are shown in FIGS. 9A to 9C. FIG. 9A shows the results of the sample only of the inorganic salt culture medium containing no YN2 strain. A peak of 1-octene is observed near 1.21. FIG. 9B shows the results of the sample of the cell suspension of YN2 strain. A peak, which is not observed in FIG. 9A, is observed near 2.38. FIG. 9C shows the results of a sample of a standard sample of 1,2-epoxyoctane. A peak corresponding to the above mentioned peak is observed near 2.38. According to the results, it was made clear that the YN2 strain converted 1-octene to 1,2-epoxyoctane.

In other words, according to the results of Examples 7 and 8, it was made clear that YN2 strain has an ability to epoxidize 1-alkene to corresponding 1,2-epoxyalkane.

Example 9

20 mg of the polymer obtained in Example 4 was dissolved in 0.2 mL of chloroform, and 10 mg of hexamethylenediamine was added thereto with cooling by ice to dissolve it. After completion of the dissolution was confirmed, chloroform was removed and then the resulting solution was subjected to a measurement with a differential scanning calorimeter (DSC; Pyris 1 mfd. by Perkin Elmer Co.; Temperature rise rate: 10° C./min). Further, another sample subjected to a reaction at 90° C. for 1 hour was similarly subjected to the DSC measurement.

Figure 10:
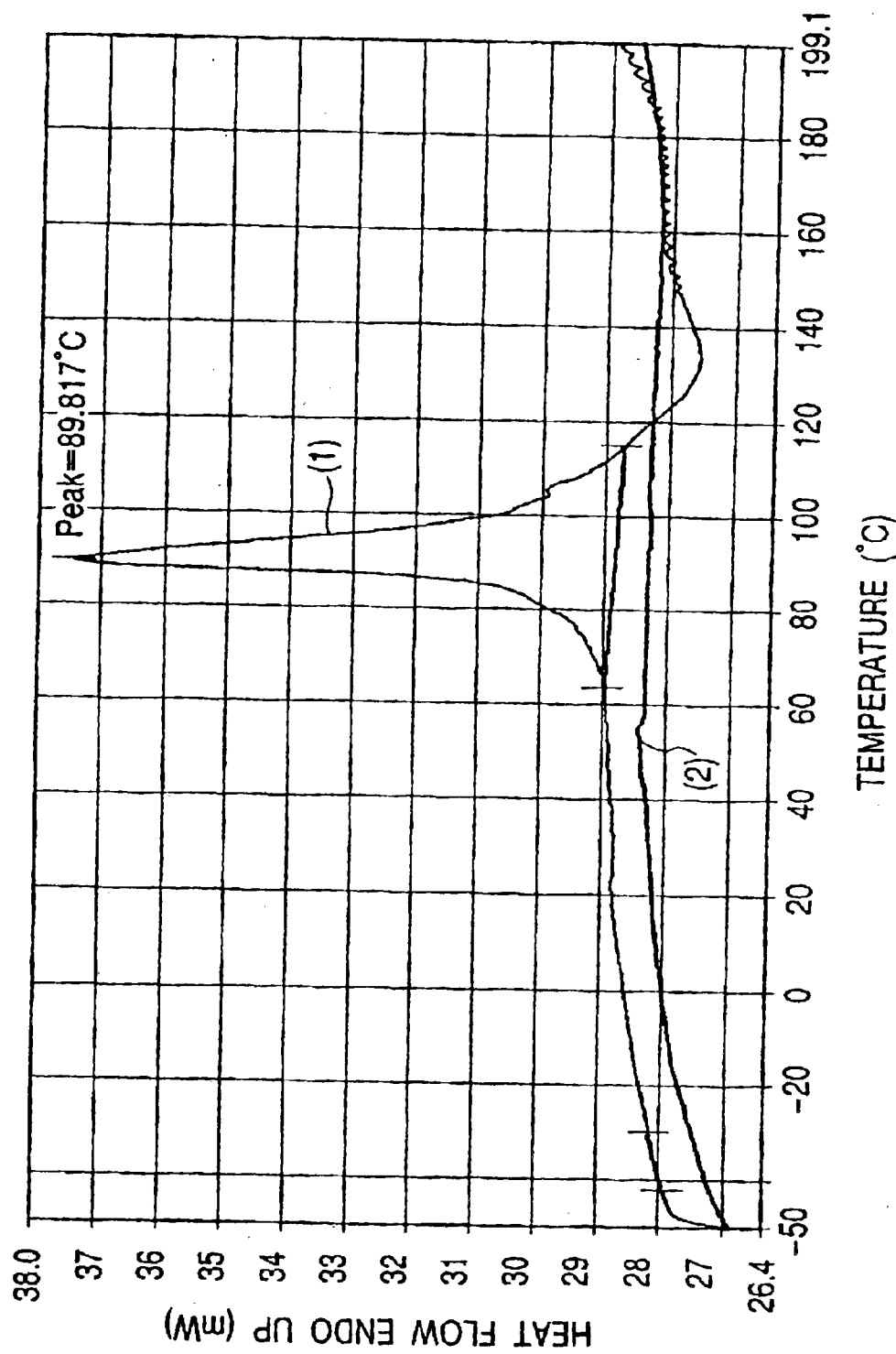
FIG. 10 is a graphical representation showing a DSC chart of the polymer described in Example 9.

The results were shown in FIG. 10. In the figure, the chart shown by (1) is of the former sample (obtained only by mixing) and the chart shown by (2) is of the latter sample (further subjected to the reaction at 90° C. for 1 hour). A clear heat generation peak was observed at near 90° C. in the chart (1), which indicates that a reaction of the epoxy groups of the polymer obtained in Example 4 with hexamethylenediamine occurs and crosslinking between polymers proceeds. On the other hand, no clear heat flow is observed in the chart (2), indicating completion of the crosslinking reaction.

Figure 11A:
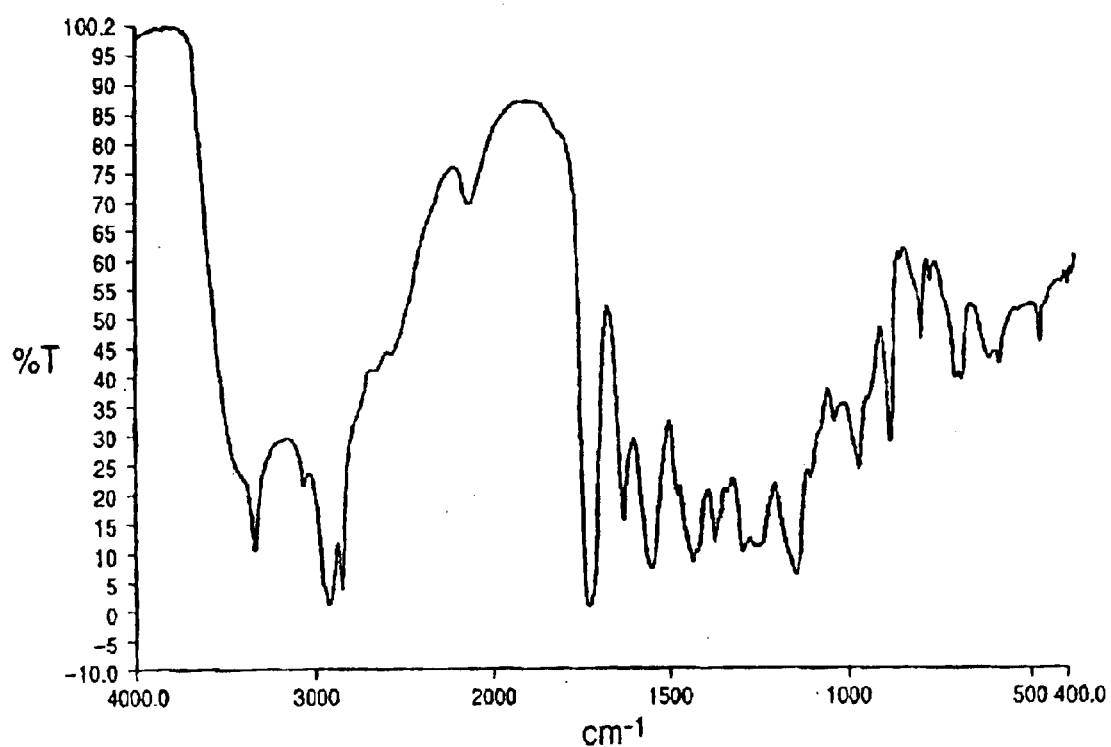
FIGS. 11A and 11B are graphical representations each showing a FT-IR chart of the polymer described in Example 9.
Figure 11B:
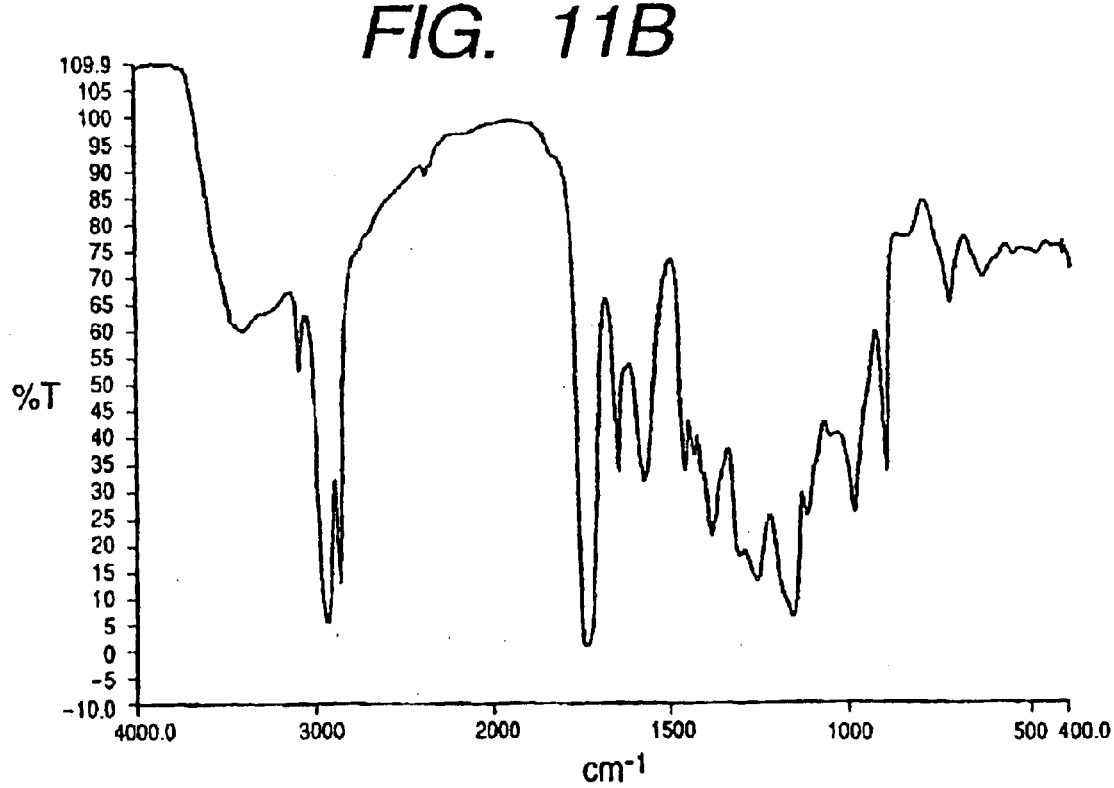

Further, using the same samples, IR absorption was measured (FT-IR; mfd. by Perkin Elmer Co., 1720X model). The results are shown in FIGS. 11A and 11B. The peak (near 3340 cm$^{-1}$) corresponding to amine and the peak (near 822 cm$^{-1}$) corresponding to epoxy group as observed in the chart of FIG. 11A disappear in the chart of FIG. 11B.

According to the above described results, it was made clear that a crosslinked polymer could be obtained by reacting, with hexamethylenediamine, a polyester having epoxy units in the side chains which was obtained by the method comprising the steps of bringing 1-alkene into contact with a microorganism having an ability to uptake and convert 1-alkene to a polyester and allowing the microorganism to convert the 1-alkene into a polyester.

Example 10

The same production experiment and evaluation was carried out as in Example 1, except that 2-nonene was used in place of 1-heptene.

Example 11

The same production experiment and evaluation was carried out as in Example 1, except that 3-nonene was used in place of 1-heptene. Dry weight of the cell and polymer obtained in Examples 10 and 11 was shown in Table 5.

TABLE 5

| Example | Cell Dry Weight (mg) | Polymer Dry Weight (mg) |
|---|---|---|
| 10 | 160 | 50 |
| 11 | 150 | 48 |

Unit analysis of the polymers obtained in Examples 10 and 11 was carried out in the same manner as in Examples 1 to 6. Area % determined by total ion chromatography (TIC) is shown in Table 6. In this case, epoxy units were not detected since the monomer units were converted by methanolysis.

TABLE 6

| Unit | Example 10 |
|---|---|
| C4 | — |
| C5 | — |
| C6 | — |
| C6= | — |
| C7 | 13.5 |
| C7= | 12.9 |
| C8 | — |
| C8= | — |
| C9 | 25.3 |
| C9= | 48.3 |
| C10 | — |
| C10= | — |
| C11 | — |
| C11= | — |
| C12 | — |
| C12= | — |

In Table 6, the symbols used for representing the units have the following meaning.

C4: 3-hydroxybutyric acid; C5: 3-hydroxyvaleric acid; C6: 3-hydroxyhexanoic acid; C6=: 3-hydroxy-4-hexenoic acid; C7: 3-hydroxyheptanoic acid; C7=: 3-hydroxy-5-heptenoic acid; C8: 3-hydroxyoctanoic acid; C8=: 3-hydroxy-6-octenoic acid; C9: 3-hydroxynonanoic acid;

C9=: 3-hydroxy-7-nonenoic acid; C10: 3-hydroxydecanoic acid; C10=: 3-hydroxy-8-decenoic acid; C11: 3-hydroxyundecanoic acid; C11=: 3-hydroxy-9-undecenoic acid; C12: 3-hydroxydodecanoic acid; and C12=: 3-hydroxy-10-dodecenoic acid.

TABLE 7

| Unit | Example 11 |
|---|---|
| C4 | — |
| C5 | — |
| C6 | — |
| C6= | — |
| C7 | 9.1 |
| C7= | 10.2 |
| C8 | — |
| C8= | — |
| C9 | 42.2 |
| C9= | 38.5 |
| C10 | — |
| C10= | — |
| C11 | — |
| C11= | — |
| C12 | — |
| C12= | — |

In Table 7, the symbols used for representing the units have the following meaning.

C4: 3-hydroxybutyric acid; C5: 3-hydroxyvaleric acid; C6: 3-hydroxyhexanoic acid; C6=: 3-hydroxy-3-hexenoic acid; C7: 3-hydroxyheptanoic acid; C7=: 3-hydroxy-4-heptenoic acid; C8: 3-hydroxyoctanoic acid; C8=: 3-hydroxy-5-octenoic acid; C9: 3-hydroxynonanoic acid; C9=: 3-hydroxy-6-nonenoic acid; C10: 3-hydroxydecanoic acid; C10=: 3-hydroxy-7-decenoic acid; C11: 3-hydroxyundecanoic acid; C11=: 3-hydroxy-6-undecenoic acid; C12: 3-hydroxydodecanoic acid; and C12=: 3-hydroxy-9-dodecenoic acid.

The polymers obtained in Examples 10 and 11 were subjected to 1H-NMR analysis (Analyzer: FT-NMR: Bruker DPX400; Determined nuclide: 1H; Solvent: heavy chloroform with TMS). The attribution of protons of methine in side chain terminals, double bonds in side chain terminals, and epoxy groups was determined according to the method described in Macromolecules, 31, pp. 1480–1486 (1998).

The mol % of respective units of which side chain is saturated, unsaturated (double-bonded) at terminal, or epoxidized at terminal was calculated based on the above described results, and shown in Table 8.

TABLE 8

| Example | Saturated Unit (%) | Unsaturated Unit (%) | Epoxy Unit (%) |
|---|---|---|---|
| 10 | 11.6 | 84.9 | 3.5 |
| 11 | 11 | 86.6 | 2.4 |

Further, the molecular weights of the polymers obtained in Examples 10 to 11 were evaluated by GPC (Tosoh Corporation HLC-8020; Column: Polymer Laboratory, PL gel MIXED-C (5 μm); Solvent: chloroform; Converted on basis of polystyrene). The results were shown in Table 9.

TABLE 9

| Example | Number-average molecular weight (Mn) × $10^5$ | Weight-average molecular weight (Mw) × $10^5$ |
|---|---|---|
| 10 | 1.7 | 4.9 |
| 11 | 1.5 | 4.6 |

Examples 10 and 11 show that strain YN2 can convert 2-nonene and 3-nonene to epoxynonane.

Although the present invention was described with 1- to 3-alkenes, the same process can be applied to produce polyester having epoxy side chains using alkene having an unsaturated bond at a position inner than position 3.

What is claimed is:

1. A method of producing a polyester containing an epoxy group in a side chain thereof using alkene as a raw material, comprising the steps of bringing alkene into contact with a microorganism having an ability to uptake alkene and convert it to a polyester and converting the alkene into a polyester containing an epoxy group in a side chain thereof by the microorganism.

2. The method according to claim 1, wherein the microorganism has (a) an ability to epoxidize and convert the alkene to an epoxyalkane compound; (b) an ability to convert the epoxyalkane compound to an epoxidized carboxylic acid; and (c) an ability to convert the epoxidized carboxylic acid to the polyester.

3. The method according to claim 1, further comprising the step of culturing the microorganism in a culture medium containing the alkene.

4. The method according to claim 3, further comprising the step of isolating the polyester produced by the microorganism.

5. The method according to claim 4, wherein the isolation step comprises recovering the polyester from the cell of the microorganism.

6. The method according to claim 1, wherein the alkene has 7 to 12 carbon atoms.

7. The method according to claim 1, wherein the polyester comprises a monomer unit having epoxy group on its side chain.

8. The method according to claim 1, wherein the alkene is 1-alkene.

9. The method according to claim 8, wherein the polyester contains at least 1 mol % of a unit represented by the chemical formula (1):

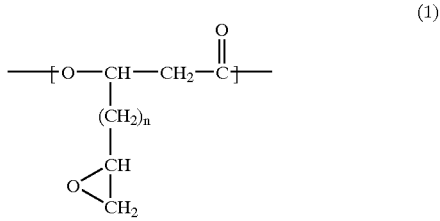

(1)

(wherein n is an integer of 1 to 7) in monomer units thereof.

10. The method according to claim 9, wherein the polyester contains at least 1 mol % of a unit represented by the chemical formula (2):

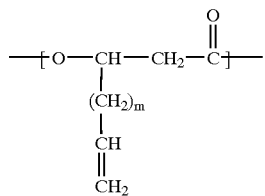

(wherein m is an integer of 1 to 7) in monomer units thereof.

11. The method according to claim 9, wherein the polyester contains at least 1 mol % of a unit represented by the chemical formula (3):

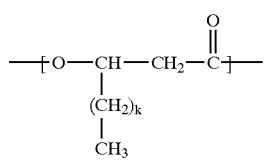

(wherein k is an integer of 0 to 8) in monomer units thereof.

12. The method according to claim 1, wherein the polyester has a number-average molecular weight of 10,000 to 1,000,000.

13. The method according to claim 1, wherein the microorganism belongs to *Pseudomonas* species.

14. The method according to claim 13, wherein the microorganism is *Pseudomonas cichorii* YN2; FERM BP-7375.

15. A method of producing a crosslinked polymer comprising reacting the polyester obtained by the method as set forth in claim 1 with a diamine compound.

16. The method according to claim 15, wherein the diamine compound is hexamethylenediamine.

17. The method according to claim 15, wherein the reaction is carried out at a temperature within the range of 50° C. to 120° C.

18. The method according to claim 15, wherein the reaction is carried out for 10 minutes to 120 minutes.

* * * * *